United States Patent [19]

Meilland

[11] Patent Number: Plant 7,668

[45] Date of Patent: Oct. 8, 1991

[54] ROSE PLANT—MEINAGRE VARIETY

[75] Inventor: Alain A. Meilland, Antibes, France

[73] Assignee: The Conard-Pyle Company, West Grove, Pa.

[21] Appl. No.: 526,988

[22] Filed: May 22, 1990

[51] Int. Cl.[5] ..... A01H 5/00

[52] U.S. Cl. ..... Plt./28

[58] Field of Search ..... Plt./28, 29

[56] References Cited

U.S. PATENT DOCUMENTS

P.P. 739 6/1947 Boerner ..... Plt. 28

P.P. 7,334 9/1990 Meilland ..... Plt. 28

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly and continuously forms attractive long lasting currant red semi-double blossoms. The plant is bushy, low, compact, and well-balanced, and exhibits vigorous vegetation. The new variety is particularly well suited for the decoration of parks and gardens. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Meinececa variety (nonpatented in the United States). The male parent (i.e., the pollen parent) of the new variety was the Lilli Marlene variety U.S. Plant Pat. No. 1,986). The parentage of the new variety can be summarized as follows:

Meinececa × Lilli Marlene.

The seeds resulting from the above pollination were sown and 96 small plants were obtained which were physically and biologically different from each other. Selective study resulted in the identificaiton of a single plant of the new variety.

The new variety meets well the needs of the horticultural industry for all uses, and is particularly well suited for growing in parks and gardens.

It was found that the new variety of Floribunda rose plant of the present invention possesses the following combination of characteristics:

(a) forms attractive long lasting semi-double blossoms which are currant red in coloration,
(b) forms vigorous vegetation,
(c) exhibits a bushy, low, compact and well-balanced growth habit, and
(d) is particularly well suited for the decoration of parks and gardens.

The new variety undergoes asexual propagation by various routes, including budding, grafting, cuttage, etc. Asexual reproduction by the above mentioned methods as performed in France shows that the characteristics of the new variety are strictly transmissable from one generation to another.

The new variety has been maned the Meinagre variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and observed during September while budded on *Rosa froebelli* understock and growing outdoors at LeCannet-des-Maures, Var, France.

FIG. 6 illustrates a specimen of a blooming flower—plan view—obverse;

FIG. 7 illustrates a specimen of a blooming flower—plan view—reverse;

FIG. 9 illustrates a specimen of a floral receptacle showing the arrangement of the stamens and pistils;

FIG. 12 illustrates a specimen of an adult main branch;

FIG. 13 illustrates specimens of leaves with three leaflets—upper (at the upper left) and under surface (at the lwor right) surfaces;

FIG. 14 illustrates specimens of leaves with five leaflets—upper (left) and under (right) surfaces;

FIG. 15 illustrates a specimen of a leaf with seven leaflets—under surface; and FIG. 16 illustrates specimens of three floral hips.

DETAILED DESCRIPTION

Figures 1, 2, 3, 4, 5, 8, 10, 11:
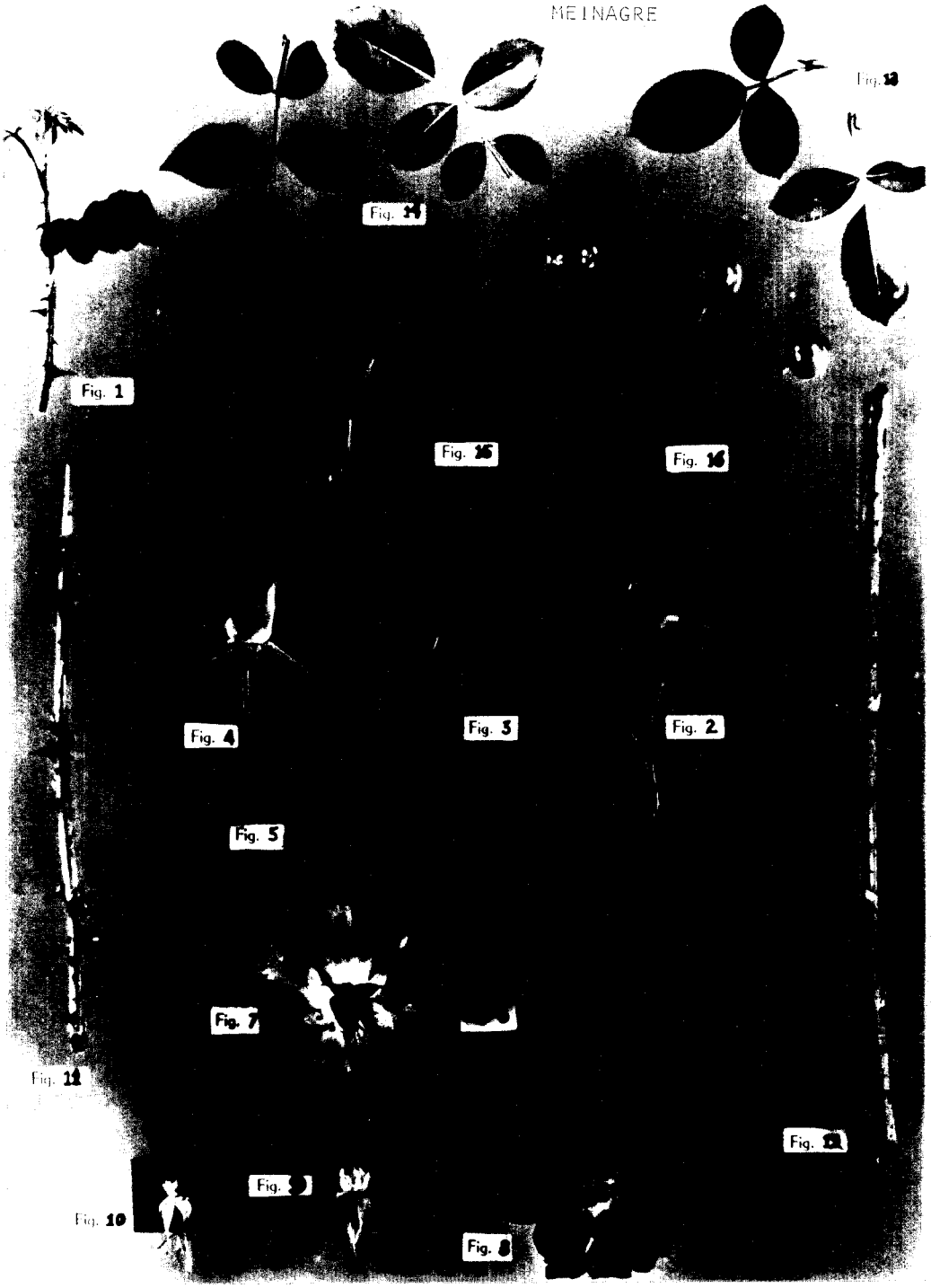
FIG. 1 illustrates a specimen of a young shoot.
FIG. 2 illustrates specimens of three buds before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 8 illustrates a specimen of a fully open flower immediately prior to petal drop—plan view—obverse.
FIG. 10 illustrates a specimen of a floral receptacle showing the arrangement of the pistols (stamens removed)
FIG. 11 illustrates a specimen of a young flowering stem.

The chart used in the identification of the colors is that of the Royal Horticultural Society (R.H.S. Colour Chart). The terminology which precedes reference to the chart has been added to indicate the corresponding color in more common terms. The description is based on two year old specimens of the new variety during September while grafted on *Rosa froebelli* understock and growing outdoors at LeCannet-des-Maures, Var, France.

Class: Floribunda.

Plant:

*Height.*—Approximately 60 to 80 cm. on average.

*Habit.*—Bushy.

Branches:

*Color.*—Young Stems: light green, Yellow-Green Group 146C, widely stained with reddish brown coloration. Adult wood: light green, Yellow-Green Group 146C.

*Thorns.*—Size: medium, Quantity: average, mixed with small prickles and glandular acicules. Color: reddish with greenish tips on young stems and pinkish-green changing to tan on adult wood.

Leaves:

*Stipules.*—Adnate, pectinate, fairly wide and linear, ending with two leaf-like appendices.

*Petioles.*—Upper Surface: Striped, reddish brown on young foliage and medium green on adult foliage with more or less glandular edges. Under Surface: light green, with a few prickles.

*Leaflets.*—Number: 3, 5, and sometimes 7. Shape: oval. Serration: single and regular. Texture: consistent. General Appearance: dense, bright foliage. Color (young foliage): Upper surface: medium green, Yellow-Green Group 146B, more or less suffused with reddish coloration. Under Surface: light green, Yellow-Green Group 146C, more or less suffused with reddish coloration. Color (adult foliage): Upper Surface: dark green, Yellow-Green Group 147A. Under Surface: medium green, Yellow-Green Group 147B.

Inflorescence:

*Number of flowers.*—Commonly 1 to 6 per stem.

*Peduncle.*—Approximately 5 to 6 cm. in length on average.

*Sepals.*—Upper Surface: tomentose and greenish, widely stained with reddish coloration. Under surface: medium green in coloration, the outer sepals have glandular edges which are only slightly appendiculated.

*Buds.*—Shape: conical. Length: approximately 3 cm. on average. Size: medium. Color upon opening: Upper surface: Velvety cardinal red, Red Group 53A, with a yellowish base. Under surface: guardsman red, Red Group 45A, with a yellowish base.

*Flower.*—Shape: cuplike and semi-double. Diameter: approximately 7 to 9 cm. on average. Color (when opening begins): Upper surface: velvety currant red, Red Group 46A, whitish at the base of the petals. Under surface: velvety currant red, Red Group 46A, suffused with medium currant red, Red Group 46B, whitish at the base of the petals. Color (when blooming): Upper surface: velvety currant red, Red Group 46A, whitish at the base of the petals. Under surface: velvety currant red, Red Group 46A, suffused with turkey red, Red Group 46C, whitish at the base of the petals. Color (at end of opening): Upper surface: medium currant red, Red Group 46B, whitish at the base of the petals. Under surface: medium currant red, Red Group 46B, suffused with dark neyron rose, Red Group 55A, whitish at the base of the petals. Fragrance: none. Lasting quality: long. Petal drop: good. Petal number: approximately 14 to 15 on average. Petal texture: consistent. Petal form: The outer petals tend to be rounded, and the inner petals tend to be oval and more or less indented. Stamen number: approximately 98 to 102 on average. Anthers: normal, straw edges with ochre. Filaments: greenish and of irregular heights. Pistils: approximately 40 to 44 on average. Stigmas: normal, bright yellow. Styles: greenish and of irregular heights. Receptacle: light green, smooth, and in longitudinal section in the shape of a pear.

Development:

*Vegetation.*—Vigorous.

*Blooming.*—Very floriferous with continuous blooming throughout the season.

*Aptitude to bear fruit.*—Good.

*Resistance to diseases.*—Very good.

*Resistance to frost.*—Good.

I claim:

1. A new and distinct variety of Floribunda rose plant characterized by the following combination of characteristics:

(a) forms attractive long lasting semi-double bloosoms which are currant red in coloration, (b) forms vigorous vegetation, (c) exhibits a bushy, low, compact and well-balanced growth habit, and (d) is particularly well suited for the decoration of parks and gardens;

substantially as herein shown and described.

* * * * *

MEINAGRE